United States Patent [19]

Hardy

[11] Patent Number: 4,890,631

[45] Date of Patent: Jan. 2, 1990

[54] EXTERNAL FIXATION DEVICE INTENDED FOR ORTHOPEDIC USE

[75] Inventor: Jean-Marie Hardy, Larches, France

[73] Assignee: Societe De Realisations Electro-Mecaniques Sorem, Toulon Cedex, France

[21] Appl. No.: 153,516

[22] Filed: Jan. 29, 1988

Related U.S. Application Data

[63] Continuation of Ser. No. 830,654, Feb. 18, 1986, abandoned.

[30] Foreign Application Priority Data

Feb. 22, 1985 [FR] France .................. 85 02577

[51] Int. Cl.⁴ .............................................. A61F 5/04
[52] U.S. Cl. ........................................ 606/59; 606/74
[58] Field of Search ............... 128/92 R, 92 Z, 92 ZZ, 128/92 Z X, 92 ZN, 69, 84 R

[56] References Cited

U.S. PATENT DOCUMENTS

| | | | |
|---|---|---|---|
| 2,055,024 | 9/1936 | Bittner, Jr. ................... | 128/92 Z |
| 3,985,127 | 10/1976 | Volkov et al. ................. | 128/92 Z |
| 4,127,119 | 11/1978 | Kronner ........................ | 128/92 Z |
| 4,185,623 | 1/1988 | Volkov et al. ................. | 128/92 Z |
| 4,273,116 | 6/1981 | Chiquet ........................ | 128/92 Z |
| 4,365,624 | 12/1982 | Jaquet .......................... | 128/92 Z |

Primary Examiner—Mickey Yu
Assistant Examiner—Michael Brown
Attorney, Agent, or Firm—Burgess, Ryan & Wayne

[57] ABSTRACT

An external fixation device for orthopedic use adapted to be used with the so-called ILIZAROV method including at least two hoops for a substantially cross-shaped attachment of pins, cross-pieces connecting the hoops in spaced relation, each cross-piece including a first end connected to one hoop and a second end connected to another hoop, a device for adjusting the length of the cross-pieces for putting under traction or compression, at least a bone fragment to which the cross-pieces connect respectively through the hoops and the pins, a first clamp device for clamping a first end of each pin, a second clamp device for clamping a second opposite end of each pin, the first clamp device and second clamp device are connected to the hoops diametrically, and a device for moving the first clamp device away from the second clamp device to tension the respective pins.

8 Claims, 4 Drawing Sheets

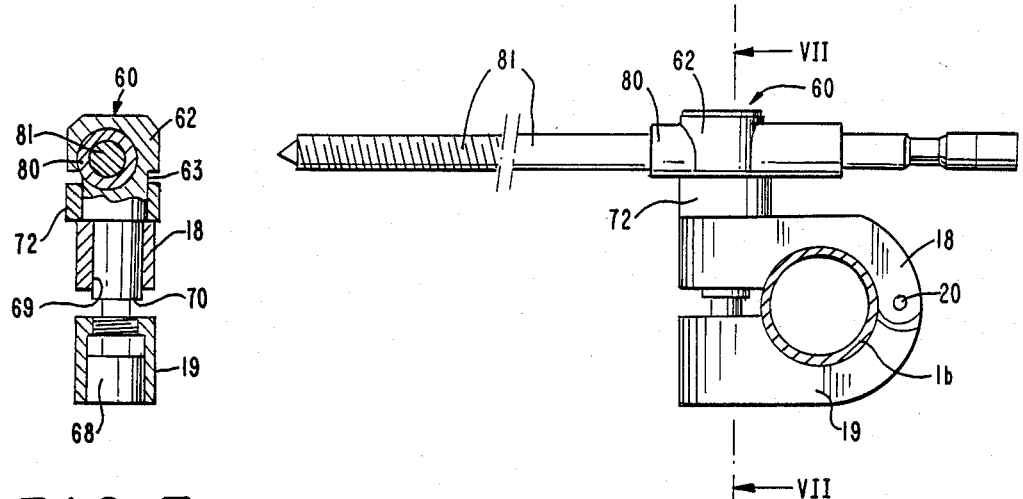
FIG. 7
FIG. 6
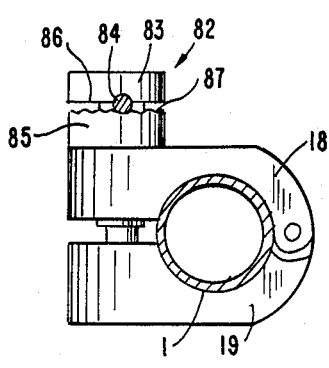
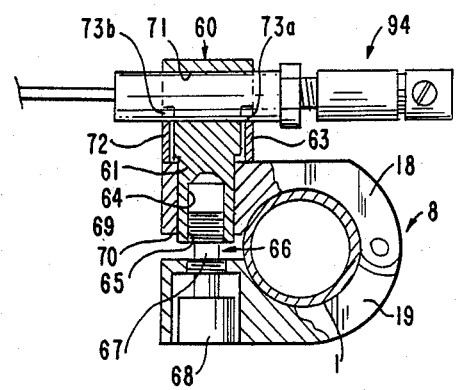
FIG. 9
FIG. 8

EXTERNAL FIXATION DEVICE INTENDED FOR ORTHOPEDIC USE

This application is a continuation of application Ser. No. 830,654, filed Feb. 18, 1986, now abandoned.

BACKGROUND OF THE INVENTION

Field of the Invention

The present invention concerns an external fixation or attachment device intended for use in orthopedic applications, and concerns, more particularly, the said device adapted for use in the method known as the ILIZAROV method.

According to this method, which is widely known, to a bone and/or bone fragment, there is associated a pair of needles or pins presenting a small-sized diameter that intersect substantially at right angles in each bone structure, respectively. Once the ends of the needles have been attached to external supports corresponding to the members to be treated, the said needles are placed under tension and the supports to which the needles are attached are interconnected together by cross-pieces having an adjustable length that comprise means for compressing or extending the whole of the said system and thus applying dynamic action(s) to the said bones or bone fragments. These braces are fixed in predetermined positions through the arrangement of holes or perforations provided at regular distances from one another upon the above-mentioned supports.

External attachment devices intended to be used in applying the ILIZAROV method are already known, i.e. devices or apparatus used for the treatment through compression-extension of fractures, for the treatment of persistently defective calluses of the long bones, or furthermore for the treatment of elongations to be operated on without bleeding, etc.

These known apparatus comprise flat section metal rings or half-rings, comprising prepositioned holes for the fixation of the cross-pieces and adapted to be interconnected to one another by solid metal rods provided with screws, nuts and lock-nuts. However, this assembly is heavy and difficult to handle due to its larger number of constitutive elements so that the apparatus is relatively unsuitable for utilization within a modern medical environment.

Furthermore, known apparatuses also present inherent drawbacks with respect to the medical-surgical point of view. Indeed, the structure of section rings or half-rings as well as the predetermined position of the perforations present on the rings or half-rings do not allow practitioners to achieve the desired accuracy of positioning, especially upon the angular plan, so that with known apparatus the method called the ILIZAROV method has not been as widely used as might have been envisaged.

In a general manner, one of the aims of the present invention is to provide an external fixation or attachment device intended for use in the orthopedic field, adapted to be used in the ILIZAROV method, which is much simpler to use than the known devices.

A further aim of the invention is to provide such device formed of a reduced number of constitutive parts, which thus facilitates transport and which, due to this fact, can be applied under difficult surgical intervention conditions.

It is yet a further aim of the invention to provide such device which overcomes the drawbacks mentioned herein-above inherent in the known devices, especially with respect to the accurate positioning of its constitutive elements relative to the bone to be treated.

Similarly, another aim of the invention is to provide said device which considerably increases the possibilities of surgical therapy due, in particular, to the adaptability of the apparatus according to the invention, to different types of cases, but also due to the ease in its fitting and removal as well as the possibilities of its adjustment.

An external fixation device for orthopedic use adapted to be used with the so-called ILIZAROV method, comprises at least two rings or hoops for the substantially cross-shaped attachment of pins or needles, with cross-pieces intended to connect the said hoops and comprising means for adjusting their length for putting a bone and/or bone fragment to which they are connected under traction or compression, respectively, means being furthermore provided for the putting under tension of the said pins or needles, are characterized according to the invention in that the hoops are produced from a tube having a circular cross-section.

According to one embodiment of the invention, the said device comprises articulated collars being able to be fixed and rendered locked in any given position of the hoops thereby allowing the fixation of braces.

According to another variant of the invention, certain of the said collars can be fixed and rendered locked in any given position of the hoops comprising means for receiving and locking in position one end of the said pins or needles.

According to another variant of the invention, the other ends of the pins or needles are attached to members immovably associated to the said collars.

Preferably, the said members comprise the said adjustable means for putting under tension the said pins or needles.

According to a further embodiment of the invention, the hoops are formed of two half-hoops connected by assembly means.

Preferably, the assembly means are constituted by notched joint-type articulations.

BRIEF DESCRIPTION OF THE DRAWINGS

The invention will become more apparent from reading the following description, given by way of non-limitative illustration with reference to the appended drawings in which:

FIG. 6 is a view taken along line VI—VI of FIG. 6;

FIG. 7 is a sectional view, along the line VII—VII of FIG. 6;

FIG. 8 is a sectional view of a collar of a device according to the invention;

FIG. 9 is a view analog to that of FIG. 5, but in respect of another embodiment;

DETAILED DESCRIPTION OF THE INVENTION

Figure 1:
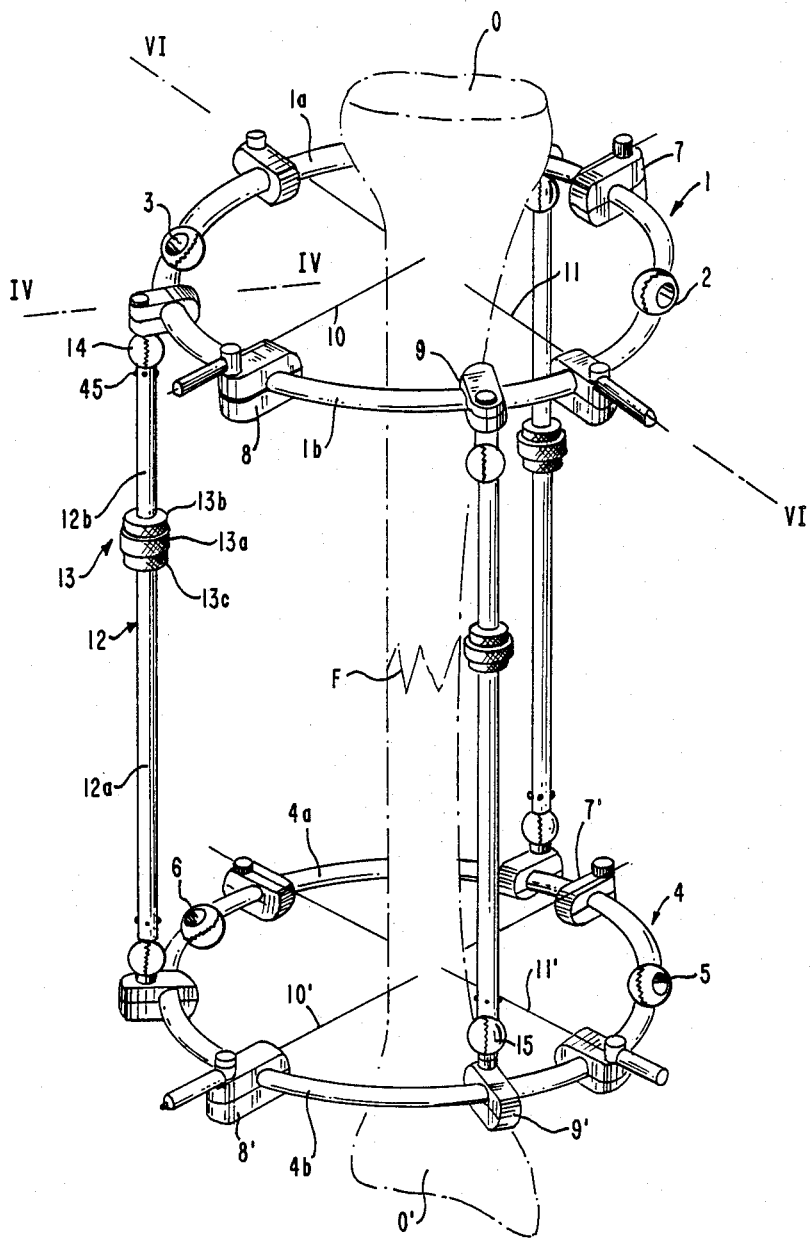
FIG. 1 is a view in perspective of a device according to the invention in its utilization state, for example, for the treatment of a fracture of a long bone.

Reference will firstly be made to FIG. 1 which illustrates the general arrangement of an external fixation device according to the invention intended for orthopedic use.

This device, adapted to be used with the so-called ILIZAROV method, comprises a first ring or hoop 1, advantageously constituted by the association through two notched articulation 2 and 3 of two half-hoops, 1a and 1b respectively, as well as a second ring or hoop, 4, also advantageously constituted by associating through notched articulations 5 and 6 two half-hoops 4a and 4b, respectively, the half-hoops 1a, 1b, like the half-hoops 4a and 4b, being produced from a tube, presenting a circular cross-section and, for example, a diameter of 12 mm.

Upon each of these hoops 1 and 4, there are mounted articulated collars which bear reference numerals 7, 8 and 9 when they are associated with the hoop 1 and 7', 8' and 9' when they are associated with the hoop 4, and they will be described in further detail herein-below.

The articulated collars such as 7 and 8 are provided for attaching to the hoop 1, pins or needles 10 and 11 which, according to the ILIZAROV method, intersect within a bony or osseous structure O (represented in mixed lines). The collars 7' and 8', associated with hoop 4, maintain, in position upon said hoop, analog pins or needles 10', and 11', also provided so as to intersect within the bony structure, for example O', opposite the structure O with respect to a fracture F in the case where the device is intended to be fitted, for example for a case of osteosynthesis. It is well understood that this indication is given by way of non-limitative illustration, taking into account the large number of possible therapeutic indications.

In the utilization conditions of the device, hoops 1 and 4 are connected to each other by three tubular braces 12, of adjustable length, each of which is constituted by a first part 12a and a second part 12b connected to each other by a system 13 provided with a threaded screw and milled nuts or octagonal nuts 13a, 13b, 13c, these two latter nuts cooperating with parts 12a and 12b, respectively, in order to control their telescopic separation.

In order to connect the braces 12 to the hoops 1 and 4, the invention foresees applying collars 9 and 9' to which are associated respectively notched joints 14 and 15 having a structure analog to that bearing references 2, 3 and 5, 6.

Figure 2:
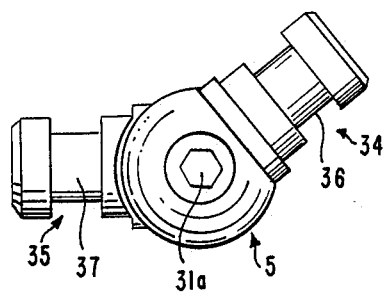
FIG. 2 is a frontal view of a notched articulation of a device according to the invention.
Figure 3:
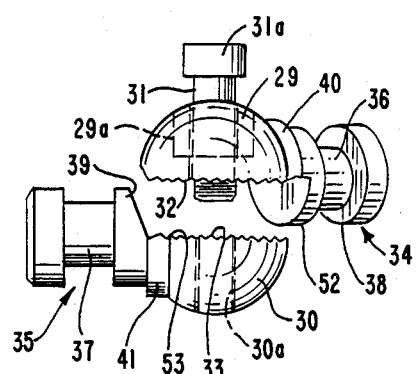
FIG. 3 is an exploded view in perspective of the said articulation according to the invention.

As illustrated in FIGS. 2 and 3, notched articulation 2, 3, 5 or 6 is comprised of two parts having substantially hemispherical bodies 29, 30 that are assembled by means of a threaded axis 31 about which they can be displaced with respect to each other in rotation, one of the hemispheres, for example that bearing reference 30, comprising an axial threading 30a whereas the other hemisphere 29 presents a recess 29a for receiving the hollow hexagonal head 31a of the threaded axis 31. The two diametrical plane faces 32, 33 each one of which is positioned opposite a hemisphere 29, 30 are toothed or milled, so that the two said half-spheres can be positioned and blocked with respect to each other in a number of stable angular positions with their faces 32 and 33 in contact.

Each of the half-spheres 29, 30 bears a radially oriented top 34, 35 intended to be inserted either into the tubular brace such as 12a or 12b, or into one of the open ends of a half-hoop forming the hoops 1 or 4, the attachment of the notched articulations to the hoops 1, 4 or to the braces 12 being ensured by the locking screw(s) 45 represented in FIG. 1, adapted to cooperate with a peripheral groove 36, 37 of each of the tips 34, 35.

The faces of these tips turned towards the half-spheres, each comprise an annular clearance 38, 39 which allows the rotation of the half-spheres 29, 30 with respect to each other without rubbing the tip 34, 35, each half-sphere comprising, furthermore, a flange segment 40, 41 that connects the half-sphere to the tip 34, 35 and which acts moreover as a positioning abutment in the constitutive tubes of the braces 12 or the hoops 1, 4. Upon the rubbing-free rotation of the two constitutive parts of the articulation with respect to each other, there is a cooperation of a flattened portion 52, 53 provided on each flange segment 40, 41 with the clearance 38, 39 of the internal face of the tip 34, 35.

The notched articulations such as 14 or 15 for connecting the braces 12 to the hoops 1 and 4 are identical to those described herein-above, with the exception that one of the tips is simply constituted by an internally threaded gun 25 and adapted to cooperate with a collar 9 or 9'.

Figure 4:
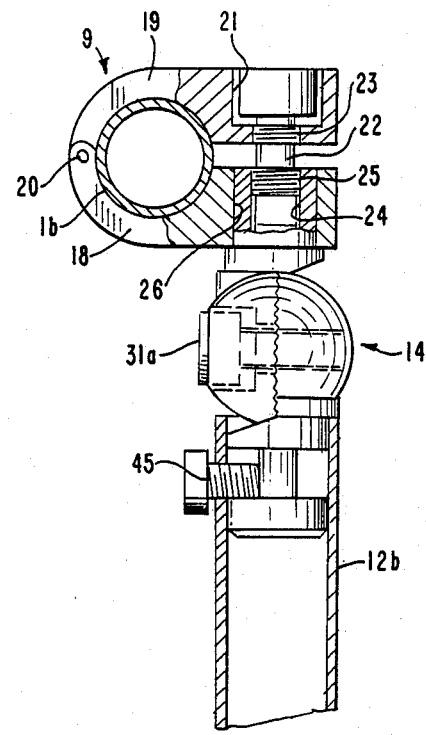
FIG. 4 is a section view along line IV—IV of the device according to the invention.

This collar such as represented in FIG. 4 comprises two jaws 18, 19 articulated between each other by a hinge 20, the jaw 19 presenting at its further end from the articulation a recess 21 for receiving the hollow hexagonal head of a rod having a threaded part 22 adapted to cooperate with one or two threads 23 at the bottom of the recess 21, on the one hand, and with the threading 24 of the gun 25 housed within a drill-hole 26 of the jaw 18.

Figure 5:
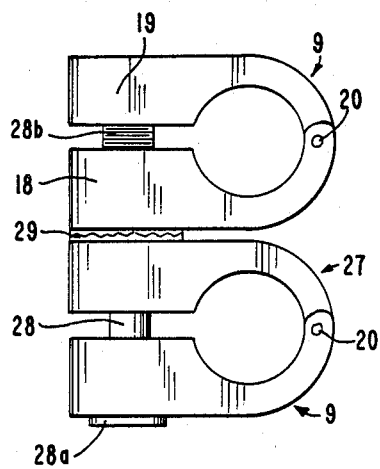
FIG. 5 is a frontal view of a clamp intended to be fitted to a device according to the invention.
Figure 5A:
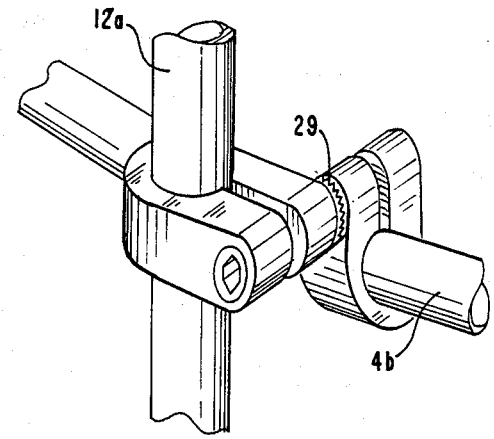
FIG. 5a is a schematic partial view in perspective of a device according to the invention fitted with a clamp according to FIG. 5.

In another embodiment, according to FIG. 5, the braces 12, advantageously constituted by rigid tubes comprising perforations (not represented), are connected to hoops 1 and 4 by a clip 27 bringing two collars together in a single piece unit such as described herein-above. Each collar is moveable about an axis 28 finishing at one end with a hollow hexagonal head 28a and at the other end by a threaded part 28b provided so as to cooperate with a screw that cannot be lost (not represented) and which is housed in the jaw of the collar 9 so as to receive the actuating head 28a. The two adjacent jaws of the collars 9 are advantageously toothed on their opposite faces and in their portions adjacent to the issues of the drill-holes passing through the passage of the axis 28, as shown in 29, so that the two collars constituting the clip can be angularly locked in secure position, with respect to each other, as well as on the braces and the hoops, by actuating the head 28a, the most simple manner being through use of an ALLEN key, the disposition thus being analog to that shown schematically in FIG. 5a.

Such an arrangement can be particularly adapted to application in surgical interventions that carry out an elongation of the bony segment, while allowing the same adjustments and angular controls as those permitted by the collar and articulation type connection represented in FIG. 4.

For the application of the ILIZAROV method the device according to the invention comprises, furthermore, means for setting in place, in the bony structure(s), pins or needles 10, 11, 10' and 11'.

The said means, shown schematically in FIG. 1, comprise articulated collars, such as described herein-above, but as shown in FIGS. 6 9, the drill-holes such as 6 in one of the jaws, and more specifically that which is not provided with a housing for receiving the actuating head of the screws, receives a piece 60 comprising a cylindrical tail 61 and a head 62, also cylindrical, connected to the tail 61 by means of a flange 63 presenting an intermediary diameter comprised between that of the head 62 and that of the tail 61. This latter tail 61 presents an axial threaded blind hole 64 which is adapted to cooperate with the threaded end 65 of a rod 66 with a non-threaded cylindrical body and which terminates by a hollow actuating head 68. The tail 61 of the piece 60 is provided so as to be housed in the drill-hole crossing through 69 of the jaw 18 in which it is adapted to rotate freely, but from which it is unable to escape due to the pins such as 70 formed upon the end face of the tail 61 after it has been introduced into the drill-hole 69.

The head 62 of the piece 60 is bored with an eye-hole 71 such as represented in FIG. 8, having an axis perpendicular to that of the tail 61 and the diameter of which has a dimension so that it prevails not only upon a portion of the head 62 but also upon a portion of the flange 63. As as can be clearly seen from FIGS. 6, 7 and 8, 63 is surrounded by a ring 72 the width or depth of which is selected so that the eye-hole 71 is completely disengaged when the ring is maintained in contact with the jaw 18 of the collar and so that the piece 60 is spaced as far apart therefrom as possible. As is clearly shown in FIGS. 7 and 8, the eye-hole 71 is partially concealed when, during release of the head 68 by using an ALLEN key, the two jaws 18, 19 are moved together. This displacement, which ensures the attachment of the articulated collar about the hoop 1 or 4, on the one hand, provokes, on the other hand, a relative movement of the head 62 of piece 60 with respect to the ring 72 so as to ensure the securing in position of the entire cylindrical portion previously introduced into the eye-hole 71 and the diameter of which corresponds to the said eye-hole. The said portion is thus confined between the internal face of the eye and two diametrically opposed zones 73a, 73b of the segment of the ring 72 opposite that bearing upon the jaw 18, as shown in FIG. 4.

According to one variant (not represented) the head 62 forms part of the hexagonal end, thus allowing release by means of a standard key or tool, for its rotary operation.

For the putting in place of the external contention means that constitute the device according to the invention, a bony structure, such as O represented in FIG. 1, is surrounded by a hoop 1 upon which are attached three collars such as those bearing reference numeral 8. In the eye-hole 71 of each of these pieces 60 associated with the collar 8 is placed a fitting sleeve 80 for a self-threading plug 81. As shown in FIG. 6, for example having a diameter of 4 mm while the diameter of the eye-hole 71 can be about 8 mm.

Figure 10:
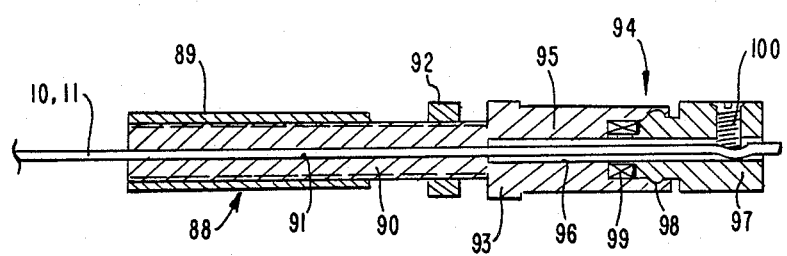
FIG. 10 is a view, on a larger scale, of a means for putting under tension a pin of a device according to the invention.

The three collars being disposed at 120° upon the hoop 1, the surgeon causes the plugs 81 to penetrate the bony structure, while only boring each time a single cortical; then he places in position with great accuracy the hoop 1 relative to the bony structure O, through manipulating the articulations such as 2 and 3 and the collars such as 8. If the angular measurements which he then takes are satisfactory, he places in position the pins or needles 10, 11, which generally have a diameter of about 1.8 to 2 mm by applying collars such as 8 to which have thus associated means 82 for supporting the said pins or needles, as shown in FIG. 9, and the elements acting both for the support and for the putting under tension of the said needles or pins, as shown in FIGS. 8 and 10. The means 82 (FIG. 9) for supporting one end of the needles or pins have a structure analog to that described herein-above for the piece 60 with the exception that the head 83, corresponding to the head 62, is bored with an eye-hole 84 having a smaller diameter while the ring 85, corresponding to the ring 72, is provided on its face 86 opposite the head 83 with notches or toes 87.

One end of a pin or needle 10, 11 being fixed within the means 82, the other end of the said pin or needle is received in an element 94, comprising an internally threaded sleeve 89 provided so as to be housed in the eye-hole 71 of a piece 60. With the sheath 89 cooperates a threaded rod 90 bored by an axial passage bore 91 for a pin or needle 10, 11 and with which is adapted to cooperate, on the one hand, a blocking nut 92 and, on the other hand, a release nut 93 of movable equipment 94.

This latter comprises a sleeve 95, with an axial passage bore 96 of the pin or needle 10, 11 integral in translation with a ring 97 through the intermediary of ratcheting lugs 98 but free in rotation from the said ring through the intermediary of bearings 99. The ring 97 is also bored axially for the passage of a pin or needle 10, 11 and is provided with two radiating bores 100 in which are housed hollow head hexagonal screws, the actuating of one of these screws deforming the pin or needle 10, 11, as can be seen in FIG. 10, in order to render it immobile with respect to the ring.

The disposition of the equipment 94 allows the translation movement of the assembly, parallel to the direction of the pin or the needle, without putting it into rotation about itself and, consequently, without any movement other than a translation movement in the bony structure through-crossed by the said pin or needle.

Once the pins or needles 10, 11 have been put in place, and this operation has been carried out with a precision to within a 5° angle, the self-threading plugs 81 are removed, the pins or needles 10, 11 are placed under tension by using elements 88, and this tension, which can be about 100 kg, is maintained, by bringing the nut 92 into contact with the sheath 89.

Operating proceeds in the same way for the putting into place of the ring 4 and the needles to which it is associated. Thus, the two hoops 1 and 4 are brought together by means of braces 12.

The presence of articulations such as 2, 3, 5, 6 upon the hoops and the articulation such as 14 and 15 on the braces, as well as the use of clamps such as 27 provided with two articulated collars produces a high degree of liberty, thereby offering the surgeon numerous possibilities of application.

Furthermore, the arrangement of the present device such as described herein-above authorizes during the evolution of the consolidation of a fracture, movements of the two hoops with respect to each other which constitutes a factor of prime importance for the obtention of satisfactory therapeutic results, particularly in interventions where it has been observed that after a certain lapse of time a defect of reduction of the fracture occurs.

The device according to the present invention is not, however, in any way limited to this type of intervention.

Figure 11:
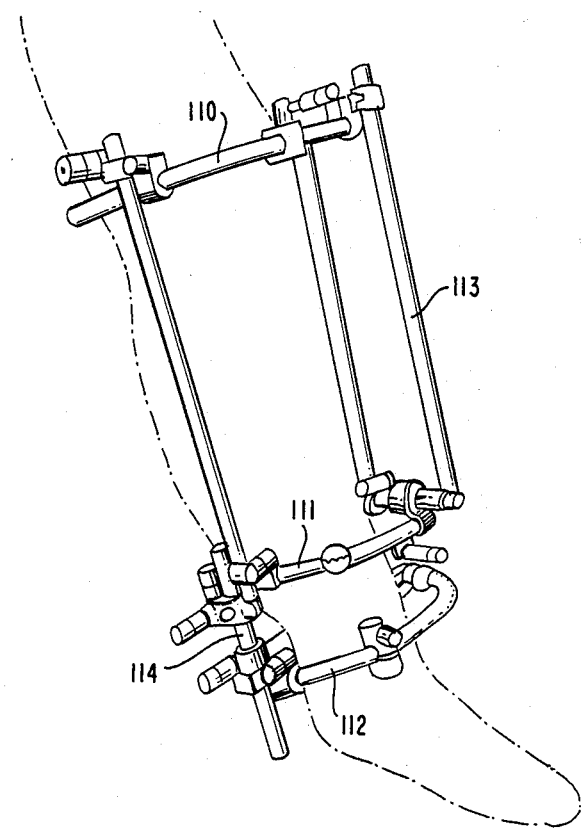
FIG. 11 is a schematic view, in perspective of a device according to the invention for another form of utilization.

Therefore, as can be seen in FIG. 11 by way of example, a device according to the invention utilizing three hoops 110, 111, 112 to which are associated, respectively, three sets of pins or needles 10, 11 and two sets of braces respectively 113 between the hoops, 110 and 111 and 114 between the hoops 111 and 112, can be applied for the treatment of low fractures to the ankle or furthermore of fractures known as bifocal fractures.

Whatever the type of intervention, the arrangement of the device according to the invention can be modified and adjusted until complete healing has been achieved, thereby further contributing to the important interest of the present device.

I claim:

1. An external fixation device for orthopedic use adapted to be used with the so-called ILIZAROV method, comprising:
   at least two hoops for a substantially cross-shaped attachment of pins,
   cross-pieces connecting said hoops in spaced relation, each cross-piece including a first end connected to one hoop and a second end connected to another hoop,
   means for adjusting the length of said cross-pieces for putting under traction or compression, at least a bone fragment to which said cross-pieces connect respectively, through the hoops and the pins,
   first clamp means for clamping a first end of each pin;
   second clamp means for clamping a second opposite end of each pin; said first clamp means and said second clamp means are connected to said hoops diametrically; and
   means for moving said first clamp means away from said second clamp means to tension the respective pin.

2. Device according to claim 1, further including articulated collars, which are able to be fixed and rendered immobile in any given position on the hoops and at least some of which allow attachment of the cross-pieces to the hoops.

3. Device according to claim 1, wherein the hoops are formed of two half-hoops connected through assembling means.

4. Device according to claim 3, wherein the assembling means are toothed articulations.

5. Device according to claim 4, wherein said cross-pieces are connected to said hoops by means of clamps provided with two articulated collars.

6. Device according to claim 1, wherein the cross-pieces having an adjustable length are connected to said hoops by means of assembling means including toothed joints.

7. Device according to claim 2, wherein said means for applying a tensioning force is mounted on at least some of said collars.

8. An external fixation device for orthopedic use adapted to be used with the so-called ILIZAROV method, comprising:
   at least two hoops for a substantially cross-shaped attachment of pins,
   cross-pieces connecting the said hoops,
   means for adjusting the length of said cross-pieces for putting under traction or compression, at least a bone fragment to which said cross-pieces are connected, respectively, through the hoops and the pins,
   characterized by means for applying a tensioning force to said pins and for maintaining said pins under tension, the means for applying and maintaining including:
   (a) a threaded sheath adapted to be introduced into the eye-hole of a piece cooperating with an articulated collar, and
   (b) equipment including:
      (i) a fixation ring for receiving an end of the pin,
      (ii) a nut cooperating with a threaded rod that cooperates with the sheath, and
      (iii) a sleeve integral with the nut and being mounted in rotation relative to the ring by means of bearings, and
   wherein the hoops are produced from a tube having a circular cross-section.

* * * * *